United States Patent [19]

Oliver

[11] Patent Number: 4,760,304

[45] Date of Patent: Jul. 26, 1988

[54] DARK FIELD COAXIAL ULTRASONIC TRANSDUCER

[75] Inventor: David W. Oliver, Schenectady, N.Y.

[73] Assignee: General Electric Company, Schenectady, N.Y.

[21] Appl. No.: 934,520

[22] Filed: Nov. 24, 1986

[51] Int. Cl.$^4$ .............................................. H01L 41/08
[52] U.S. Cl. ..................................... 310/335; 73/628; 73/642
[58] Field of Search ................................ 310/334–337, 310/369; 73/628, 632, 641, 642, 644

[56] References Cited

U.S. PATENT DOCUMENTS

| | | | |
|---|---|---|---|
| 4,481,822 | 11/1984 | Kubota | 73/642 X |
| 4,503,708 | 3/1985 | Kino et al. | 73/628 |
| 4,576,048 | 3/1986 | Glenn | 310/335 X |
| 4,674,334 | 6/1987 | Chimenti et al. | 73/628 X |

FOREIGN PATENT DOCUMENTS 0922622  4/1982  U.S.S.R. .................. 73/628

OTHER PUBLICATIONS

E. J. Chern et al., "Ultrasonic Characterization of Surface Flaws Using Oblique Angle Backscattering Technique", *Proceedings of 14th Symposium on NDE*, Apr. 1983.
E. J. Chern, "Surface Flaw Characterization Using Ultrasonic Backscattered Satellite Pulse Technique", *Review of Progress in Quantitative NDE*, vol. 4A, Plenum, 1985, pp. 569–576.
M. A. Breazeale et al., "Interaction of Ultrasonic Waves Incident at the Rayleigh Angle Onto a Liquid–Solid Interface", *Jr. of Appl. Physics*, vol. 48, Feb. 1977, pp. 530–537.

*Primary Examiner*—Mark O. Budd
*Attorney, Agent, or Firm*—Donald R. Campbell; James C. Davis, Jr.; Paul R. Webb, II

[57] ABSTRACT

A dark field ultrasonic transducer is constructed with an outer annular spherical or conical transducer element and an inner spherical element. The outer annular element is excited and insonifies a small portion of a part surface near a discontinuity or crack with longitudinal waves or with surface waves. The inner dark field element is not focused to be sensitive to either reflected sound or waves reradiated from the surface waves, but detects sound scattered from surface discontinuities such as a crack edge. When surface waves strike a crack edge and restrike it after reflection from the bottom of the crack, two pulses are received and the time delay between them is a measure of crack depth. The crack shape and crack depth profile are determined as the part is scanned.

15 Claims, 10 Drawing Sheets

DARK FIELD COAXIAL ULTRASONIC TRANSDUCER

BACKGROUND OF THE INVENTION

This invention relates to ultrasonic transducers for nondestructive evaluation and their fabrication, and especially to dark field transducers to inspect a solid part for flaws and cracks.

Several NDE techniques such as eddy current, fluorescent penetrant, magnetic particle, and ultrasonic surface wave, exist for locating near surface cracks in parts. With some of these it is possible to measure crack length and to measure average crack depth. It is desirable, in addition to determining crack shape, to measure crack depth along the crack in order to make cost effective part rejection decisions and to provide information for fatigue predictions. Existing methods of NDE do not provide capability for measuring crack depth profiles, and there is a need to estimate the size of other types of surface flaws.

In the field of optics, dark field illumination is known in which the illuminating beam is a hollow cone of light; the oject is viewed with a center lens which collects scattered light. The principle has not been applied to ultrasonic transducers, however.

SUMMARY OF THE INVENTION

An object of the invention is to determine surface irregularities, including crack depth profile, nondestructively using dark field coaxial ultrasonic transducers.

Another object is to provide dark field coaxial ultrasonic transducers using longitudinal and surface wave insonification, and having an inner dark field element to detect ultrasonic scattering resulting from mode conversion at a surface discontinuity or from scattering from the discontinuity at angles near but not including 180°, i.e. not including backscattering.

Another object is the provision of a method of fabricating a sphere-cone embodiment of a dark field transducer from thin piezoelectric film.

The dark field ultrasonic transducers are comprised of only two coaxial transducer elements, an outer annular transmitting element and inner detecting transducer element. They are constructed for insonification of the surface with longitudinal waves or with surface waves, or with both. The specific embodiments follow from the manner in which reflection, refraction, and mode conversion vary with the angle of incidence of the longitudinal wave in the fluid. At an angle of incidence greater than the shear critical angle (see FIG. 2) sound is totally reflected and neither shear waves or longitudinal waves are transmitted into the solid part. When the angle of incidence is increased further to the Rayleigh critical angle, a surface wave is generated and propagates along the solid surface. The surface wave reradiates into the fluid as longitudinal waves, but there is an apparent shift in the apparent point from which the longitudinal waves leave the surface known as the Schoch displacement.

These dark field transducers have an outer annular element which is excited and emits acoustic waves that are incident on the surface of the solid body at an angle such that reflected sound waves from the surface do not impinge on the inner element. The inner transducer element is spherical and has its focal point on or close to the surface of the solid body and detects sound scattered and reradiated from surface discontinuities and cracks while being insensitive to any reflected longitudinal waves or to reradiated longitudinal waves from surface waves.

A dark field transducer for longitudinal insonification has an outer element with an angular extent between an inner angle greater than the shear critical angle and an outer angle less than the Rayleigh critical angle, whereby incident longitudinal waves are totally reflected.

The principal embodiments are dark field transducers for surface wave insonification. The outer transducer element is spherical or conical. The former has an angular extent from an inner angle greater than the shear critical angle to an outer angle greater than the Rayleigh critical angle; incident longitudinal waves are converted to surface waves that propagate inwardly along the surface of the solid body. The inner and outer elements are confocal or nonconfocal. The sphere-cone transducer configuration has a conical outer element to generate plane waves that are incident on the surface of the solid body at an angle equal to the Rayleigh critical angle.

Another feature of the invention is that the diameter of the surface wave generation ring is desirably less than or equal to the Schoch displacement, to prevent significant leakage of surface wave energy back into the fluid as longitudinal waves.

The invention also encompasses a system to detect the shape and crack depth profile of cracks in a part, preferably using a surface wave dark field transducer. Surface waves generated on the part are scattered upon encountering a crack edge, reradiating as a first longitudinal wave and generating a surface wave which reflects from the bottom of the crack and returns to the crack edge and reradiates as a second longitudinal wave. The inner dark field transducer element detects the first and second longitudinal waves reradiated from the crack edge and generates voltage pulses. Means are provided to determine the time delay between these pulses and thus crack depth at locations along the crack length as the part is scanned.

Another aspect of the invention is a method of fabricating a sphere-cone dark field ultrasonic transducer using thin piezoelectric polymer film such as PVDF. A tool with which the thin film is shaped is made by placing a metal ball at the bottom of a cone in a mold and filling the bore and connecting portion of the cone with material such as epoxy. After curing the epoxy the tool is removed from the mold.

DETAILED DESCRIPTION OF THE INVENTION

Figure 1:
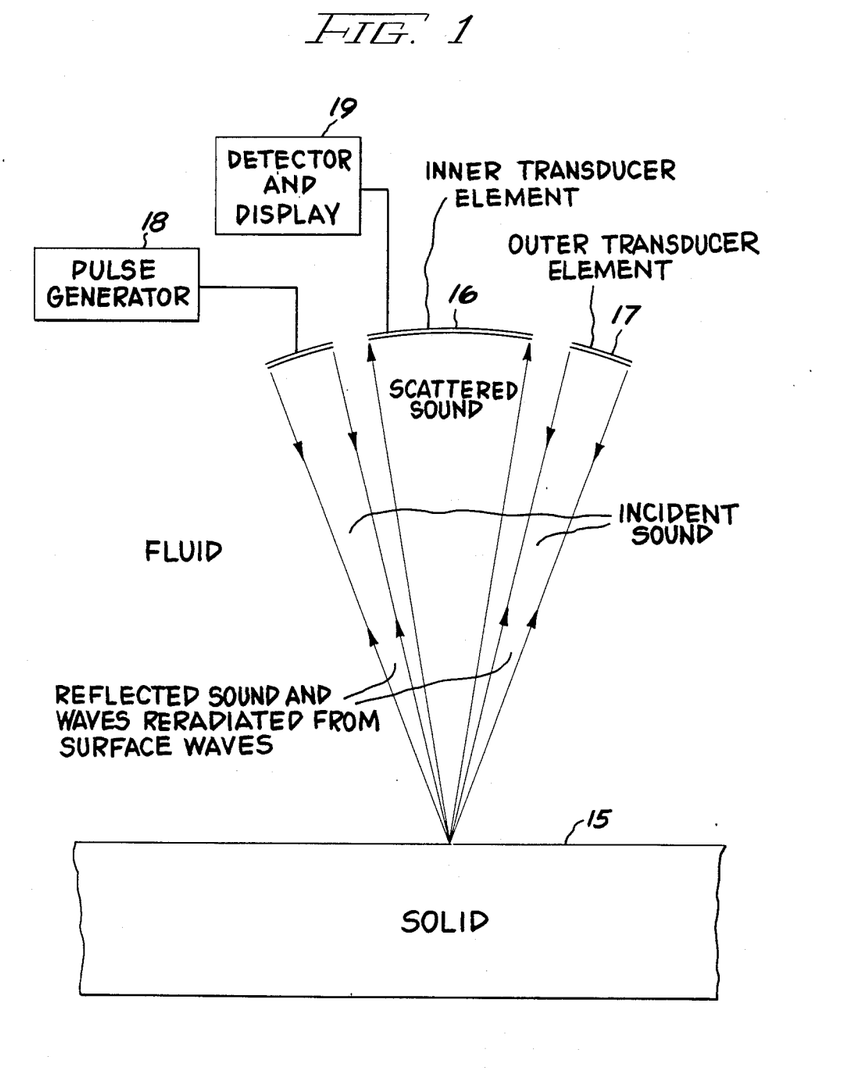
FIG. 1 is a system diagram illustrating features of a dark field ultrasonic transducer system.

The dark field ultrasonic transducers are noncontacting and use an ambient fluid, which may be water, about the solid part 15 to be inspected. The dark field transducers consist of two coaxial transducer elements as shown in FIG. 1, an inner transducer element 16 and an annular outer transducer element 17. Both elements have a thin central piezoelectric layer and thin metallic electrodes on both surfaces. The outer annular element 17 is connected to a pulse generator 18 or other excitation source, and insonifies a small portion of the part surface near a discontinuity or crack with longitudinal waves or with surface waves. The inner dark field element 16 is not focused to be sensitive to either reflected sound or waves reradiated from surface waves. Inner transducer element 16 is connected to a detector, processor and display 19, and detects scattered sound. The ultrasonic scattering detected by the dark field element 16 results from mode conversion at a surface discontinuity or from scattering from the discontinuity at angles less than 180°. The inner and outer transducer elements 16 and 17 of this transducer configuration are spherical, coplanar, and confocal. The elements are focused on the sample surface at the discontinuity or crack edge.

Figure 2:
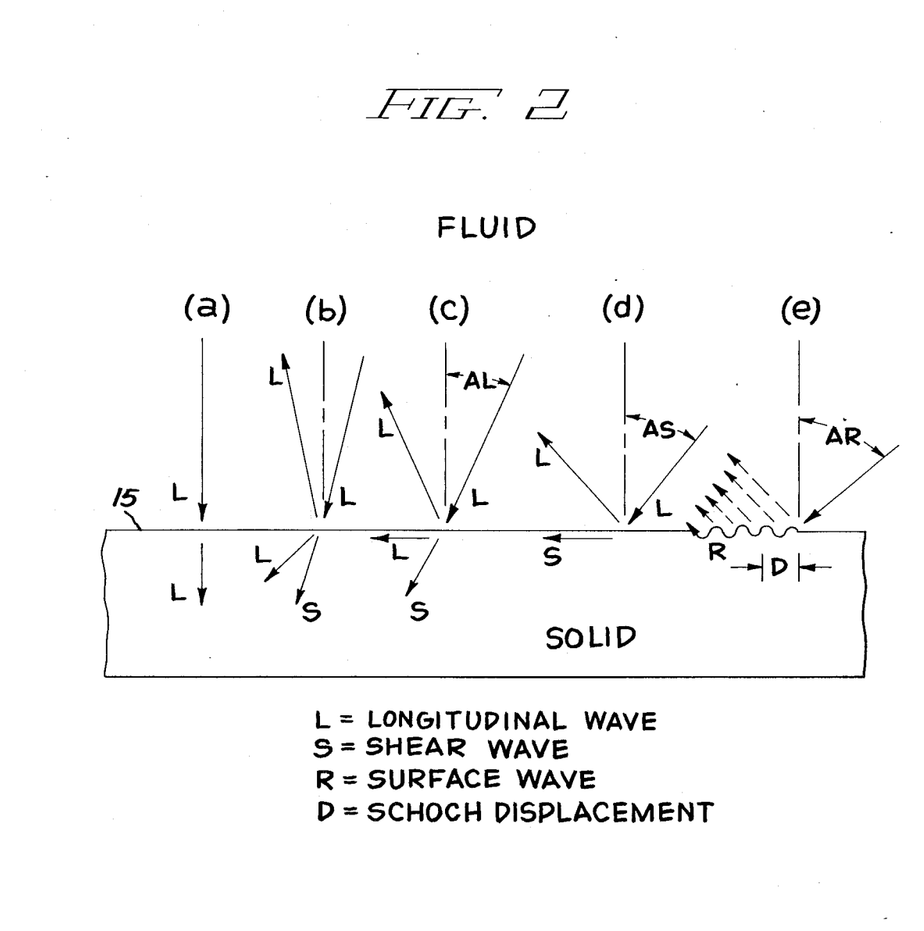
FIG. 2 shows the manner in which reflection, refraction, and mode conversion vary with the angle of incidence of the longitudinal acoustic wave in the fluid.

The illustrative embodiments of a dark field transducer in FIGS. 3-8 follow from the manner in which reflection, refraction, and mode conversion vary with angle of incidence of the longitudinal wave in the fluid, as shown in FIG. 2. FIG. 2(a) shows a longitudinal wave L, incident normal to the surface, and transmitted into the solid as a longitudinal wave. FIG. 2(b) shows an incident angle less than the critical longitudinal angle, AL, resulting in transmission of both shear waves S and longitudinal waves into the solid. In FIG. 2(c) the incident longitudinal wave is at the critical longitudinal angle, AL, where longitudinal propagation in the solid ceases and the transmitted wave has become a shear wave. When the incidence angle is increased further to the shear critical angle, AS, sound is totally reflected as shown in FIG. 2(d). The shear wave does not leave the surface of the solid. When the angle of incidence is increased further to the Rayleigh critical angle, AR, a surface wave R propogates along the solid surface. As the surface wave propogates in the presence of the fluid, it reradiates into the liquid as a longitudinal wave. This reradiated wave, shown in FIG. 2(e) as a dashed arrow, interferes with the reflected longitudinal wave. The result is a lateral shift in the apparent point from which the longitudinal waves leave the surface, Schock displacement D. Refer to M. A. Breazeale et al, Jr. of Applied Physics, Vol. 48, February 1977, pp. 530-537.

The critical angles for a superalloy, Rene 95, and water are approximately: AL=13.6°, AS=28.8°, AR=31.2°. For many materials there is no more than three or four degrees difference between AS and AR.

Figure 3:
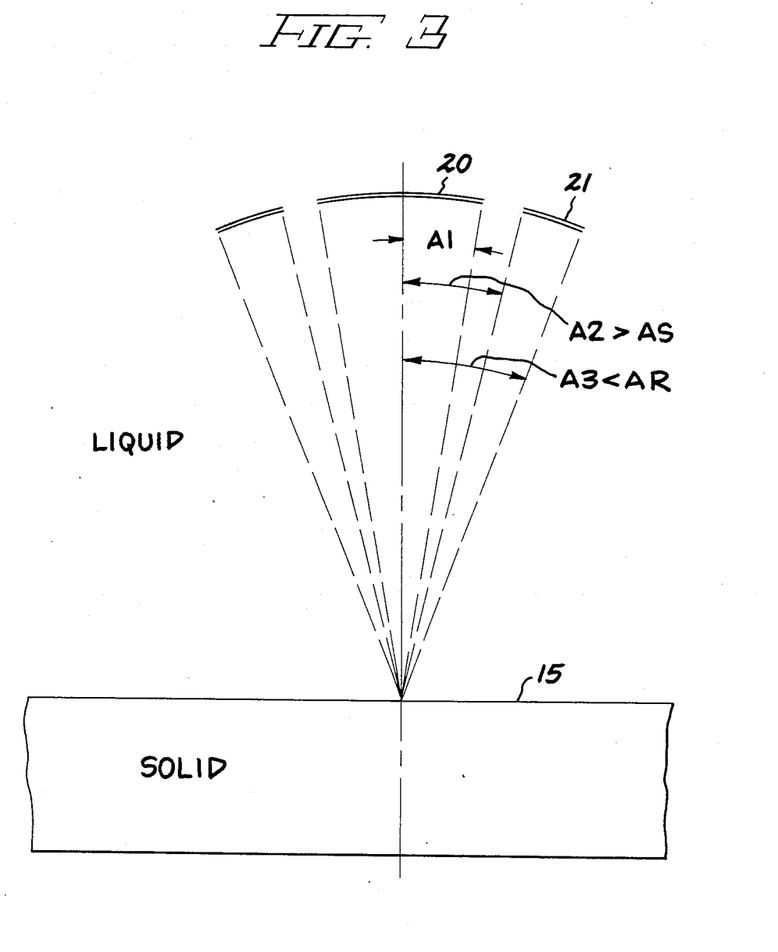
FIG. 3 shows a dark field transducer for longitudinal insonification.

A dark field transducer for longitudinal insonification is shown in FIG. 3. The inner, spherical, detecting transducer element 20 is limited in angle to A1; the outer, annular, spherical, transmitting transducer element 21 occupies an angular sector between inner and outer angles A2 and A3. When A3 is made less than the Rayleigh critical angle AR there is longitudinal excitation. When A3 is made less than AR and A2 is made greater than the shear critical angle AS, there is no propogation into the solid body 15 and the dark field transducer is sensitive primarily to surface discontinuities. The two transducer elements 20 and 21 are confocal, i.e. the focal points are at the same point. To explain further, acoustic waves emitted by annular outer element 21 are totally reflected at the surface of body 15 at an angle larger than AS and thus are not detected by the inner dark field element 20. Longitudinal waves incident on a surface discontinuity are scattered in many directions and the scattered sound is detected by inner transducer element 20. Longitudinal waves incident on a crack edge (as in FIG. 4) are scattered by the crack edge; some of the acoustic energy is detected by inner element 20 and some travels to the bottom of the crack and back up again to the crack edge where it is scattered so that a satellite pulse is generated by the inner piezoelectric element. The time delay between the two voltage pulses is a measure of crack depth at that location.

Figure 4:
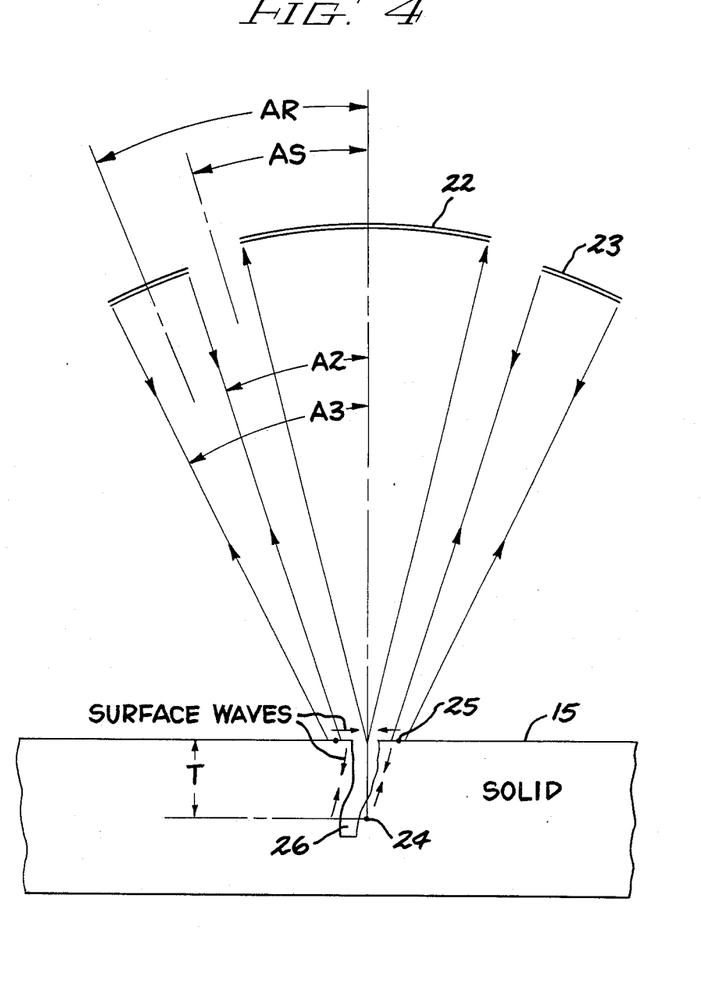
FIG. 4 is a non-confocal dark field transducer for surface wave insonification.

A first embodiment of a dark field transducer for surface wave insonification is illustrated in FIG. 4. Inner element 22 and outer annular element 23 are both spherical and are coaxial but are not coplanar. The latter helps to decouple the inner element from the outer. In this case angle A2 is made larger than the shear critical angle AS so that no rays propogate into the solid part 15, and angle A3 is made larger than the Rayleigh critical angle AR so that surface waves will be generated on the solid. The surface waves are indicated by arrows. The inner and outer elements 22 and 23 are non-confocal. The focal point of inner element 22 is on the surface of solid part 15, and the focal point 24 of outer element 23 is placed a short distance below that of the inner element and the surface of the part. This results in the generation of a ring of surface waves which propogate inwardly on the surface through the focus of the inner element 22. The maximum diameter of the surface wave generation ring is indicated at 25.

The incident surface wave energy is scattered when it encounters a sharp discontinuity, like the edge of a surface crack 26, reradiating as longitudinal waves and generating a surface wave which travels down the crack and reflects from the bottom of the crack, returns to the crack tip, and reradiates as a longitudinal wave. Two pulses are received by the inner detecting element 22 from the crack edge, a first pulse when the incident surface wave excitation hits the crack edge, and a second satellite pulse when the surface wave traveling down the crack and then back up again strikes the crack edge. The time delay between these pulses (see FIG. 13) is a measure of crack depth at a particular location along the crack length.

Figure 5:
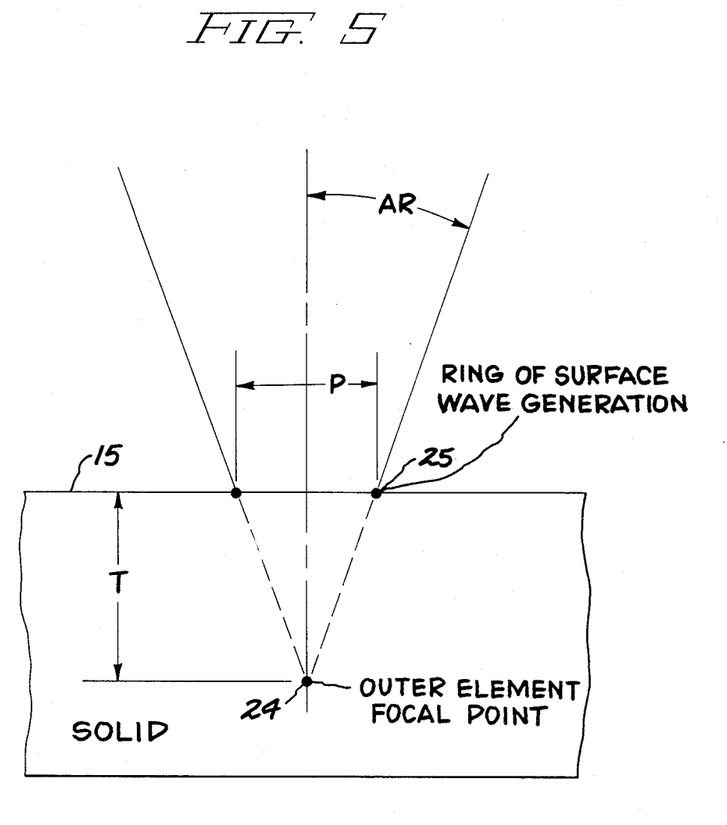
FIG. 5 is a diagram to explain selection of the diameter of the surface wave generation ring in FIG. 4 to be less than the Schoch displacment.

Since the surface waves leak energy back into the fluid as longitudinal waves, it is desirable that their propagation distance be small enough that intensity is high but large enough for good decoupling between the inner and outer elements 22 and 23. This is insured by selecting the diameter of the surface wave generation ring 25 to be less than or equal to the Schoch displacement D. The configuration is shown in FIG. 5, where P is the diameter of the ring 25 of surface wave generation and P is less than or equal to the Schoch displacement D. The ring diameter P and the Rayleigh critical angle AR determine the distance T between the focal point of the inner element 22 and the outer element 23 (T=P/2 tan AR).

The dark field ultrasonic transducer may also be employed with continuous excitation. A more complete analysis of a pulsed transducer shows that the inner dark field transducer element 22 responds to several excitations. There is cross-coupling, electrical and mechanical, with the initial pulse from the outer element 23. The reflected sound and waves reradiated from surface waves cause an output even though the inner element is not in focus for these excitations. The two pulses received by the element from the crack edge have been described. In the case of continuous excitation there is no time separation between the four received signals. The first two of these, cross-coupling and reflected or reradiated signals, are minimized by the transducer design and may be balanced out by operation in a bridge circuit such as a balanced hybrid. The depth information is then obtained by examining the interference of the first crack edge signal and the satellite crack edge signal as frequency is swept.

Figure 6:
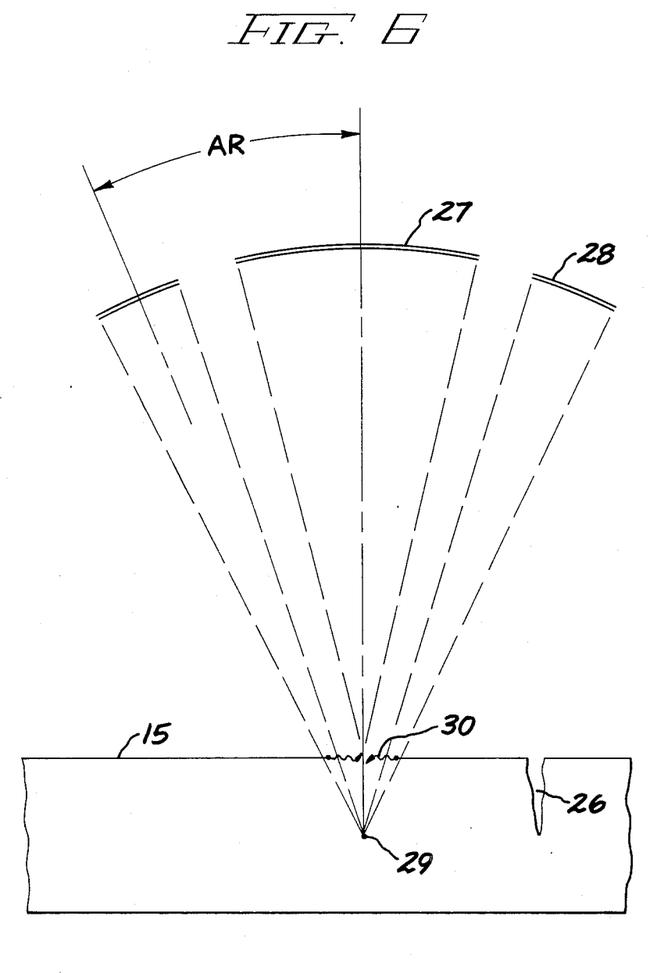
FIGS. 6 and 7 show alternate embodiments of dark field transducers which have spherical elements and generate surface waves.

FIG. 6 illustrates another embodiment of a dark field ultrasonic transducer for surface wave insonification. Inner and outer transducer elements 27 and 28 are spherical, non-confocal, and coplanar. The outer transducer element 28 has an angular extent between an inner angle greater than the shear critical angle of the solid and an outer angle greater than the Rayleigh critical angle. Inner element 27 is focused on the surface of part 15 and outer annular element 28 has an offset focal point 29 close to the surface of the part. When the outer element 28 is excited and emits acoustic waves, surface waves 30 are generated on the surface of the part. The diameter of the surface wave regeneration ring is preferably less than the Schoch displacement.

Figure 7:
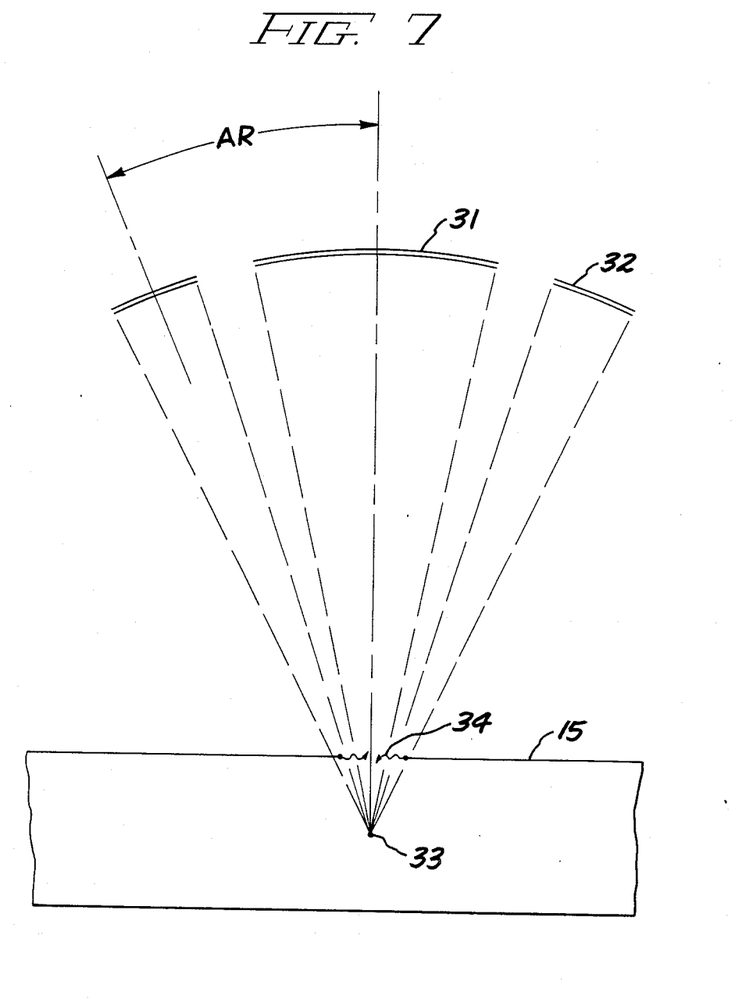

FIG. 7 shows a confocal spherical embodiment of the dark field transducer which generates surface waves. Inner and outer transducer elements 31 and 32 are spherical and coplanar, and have a common focal point 33 which is close to the surface of part 15 so that a ring of surface waves 34 is generated and its maximum diameter is again made less than the Schoch displacement. An advantage of the FIG. 7 transducer compared to FIG. 6 is that the surface wave trains propagating from the circumference toward the center of the ring are in step and constructively interfere to maximize the insonification at the center of the ring.

Figure 8:
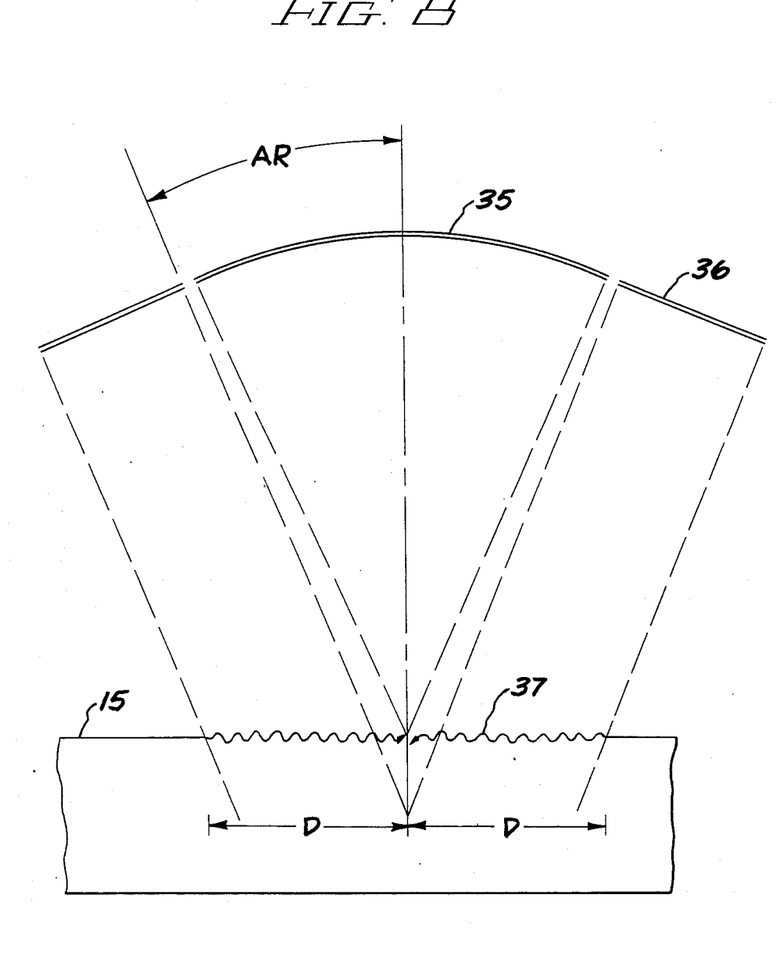
FIG. 8 shows a sphere-cone dark field transducer for more efficient surface wave insonification.

Referring to FIG. 8, the preferred embodiment of a dark field transducer to generate surface waves for flaw characterization has a spherical inner transducer element 35 and a coaxial, annular, conical outer element 36. The inner element 35 is focused at or just below the surface of part 15. Conical outer element 36 is tangent to or coplanar with the edge of inner element 35, and its inner edge typically is at an angle equal to or greater than the Rayleigh critical angle AR. Conical outer element 36 transmits plane waves; these are incident on the surface of part 15 at an angle equaling or exceeding AR so that the incident acoustic waves are converted to surface waves 37 which propogate inwardly toward the focus of inner element 35. This acoustic lens configuration more efficiently converts the incident beam into surface waves. All sound waves that create Rayleigh waves stay in phase and this dark field transducer fully uses the outer transducer element 36. The diameter of the surface wave generation ring, measured from the point where the ray from the outer edge of conical element 36 is incident on the sample surface, is no greater than the Schoch displacement.

Figure 9:
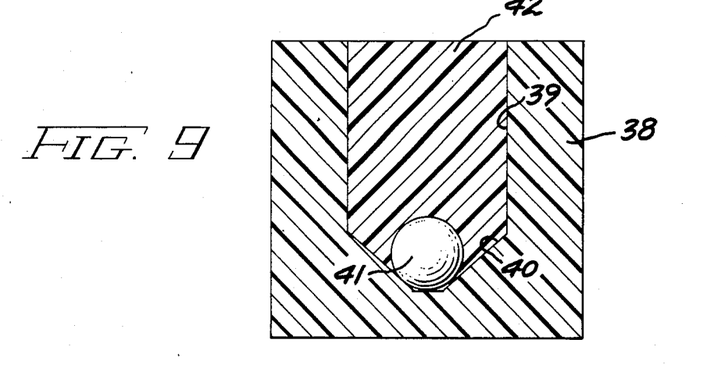
FIG. 9 is a cross sectional view of a mold to make a tool with which to manufacture the sphere-cone transducer.
Figure 10:
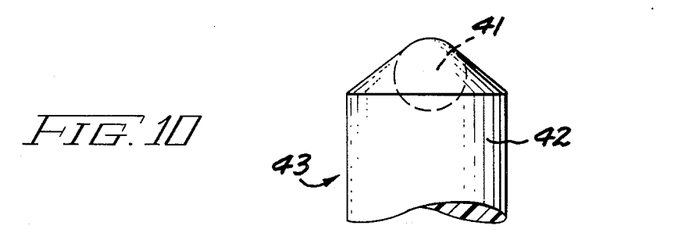
FIG. 10 is a side view of the foregoing tool.
Figure 11:
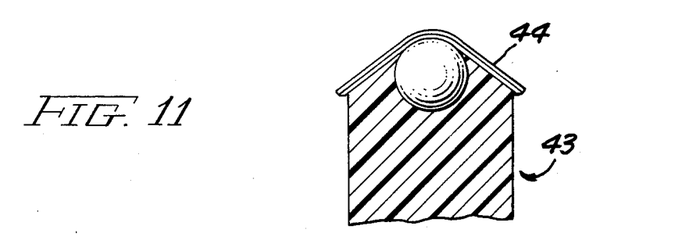
FIG. 11 illustrates stretching thin piezoelectric polymer film over the tool to form a dark field transducer.

A method of fabricating such a sphere-cone dark field transducer from thin piezoelectric polymer film is explained with reference to FIGS. 9–11. High frequency ultrasonic transducers, greater than 10 MHz and up to 45 MHz, are made with PVDF (poly vinylidene di fluoride) piezoelectric elements. The film is very thin and coated with a very thin layer of medal. The polymer film is shaped and given the desired curvature using the special tool shown in these figures.

A Teflon ® mold 38 has a cylindrical bore 39 leading to a conical cavity 40. A metal ball bearing 41, say ¼" in diameter, is placed at the bottom of the cone and the cylindrical bore and connecting portion of the conical cavity are filled with a filler material 42 such as thermosetting epoxy resin. After curing and hardening the epoxy, the mold 38 is removed leaving the tool 43 which has the metal ball embedded in a conical epoxy surface. The end of tool 43 has the desired sphere-cone shape. Metal is selectively removed from the thin coated PVDF film 44 to delineate the electrodes and inner and outer transducer elements, and the film is stretched over the end of tool 43 to shape the transducer and give it the desired curvature. A backing material is now applied to one surface of the transducer.

Figure 12:
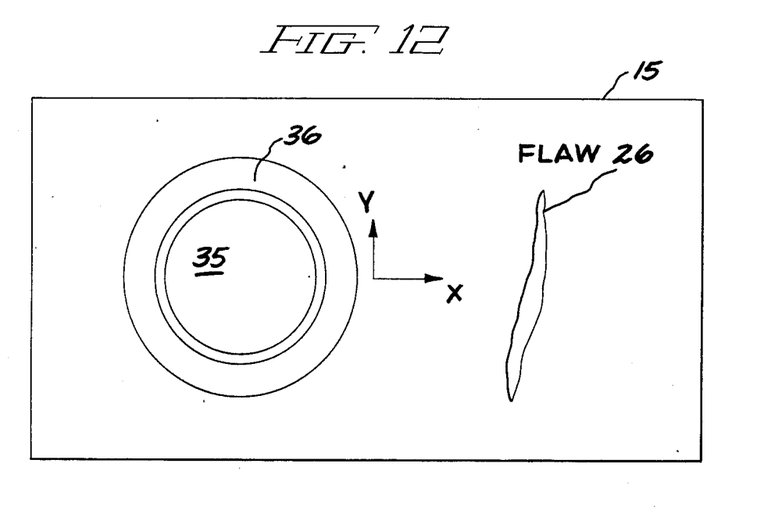
FIG. 12 illustrates scanning a part which has a surface-breaking crack.
Figure 13:
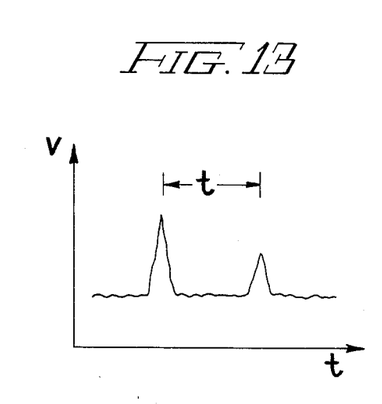
FIG. 13 shows a received signal and pulses indicating the top and bottom of a crack in the part.

FIG. 12 has a top view of the dark field transducer for surface wave insonification having the spherical inner element 35 and conical, annular outer element 36, and shows scanning the part 15 to inspect it for surface irregularities and cracks. The shape of the crack is determined and crack depth is measured along the crack length; this information is used in making part rejection decisions and for fatigue predictions. As the dark field transducer is scanned, say, in the X direction at a given Y coordinate, a first pulse is received by inner detecting element 35 when the incident surface wave excitation hits the left crack edge, and a second satellite pulse when the surface wave traveling down the crack and then back up strikes that crack edge. The received signal is seen in FIG. 13. Crack depth is derived from the time delay t between these two pulses. As the transducer is moved to the right, the right hand crack edge is detected and there are two more voltage pulses in the received waveform.

Figure 14:
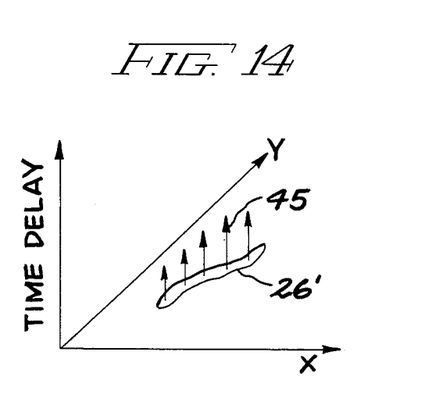
FIG. 14 illustrates one type of display of the crack shape and crack depth along its length.

The crack shape is determined by plotting the location of the larger voltage pulse in each set of two pulses. One type of display is illustrated in FIG. 14 where the shape of the crack at the surface is depicted at 26'. Time delays are plotted vertically and indicated by arrows 45 at various locations along the crack length. The crack depth profile is the envelope of these arrows.

While the invention has been particularly shown and described with reference to several preferred embodiments, it will be understood by those skilled in the art that the foregoing and other changes in form and details may be made without departing from the spirit and scope of the invention.

The invention claimed is:

1. A dark field ultrasonic transducer for inspecting a solid body comprising:

an inner detecting transducer element and a coaxial, annular, outer transmitting transducer element;

said outer transducer element having an angular extent to emit acoustic waves that are incident on the surface of said solid body at an angle greater than the shear critical angle of said solid such that neither shear waves nor longitudinal waves are transmitted into said body;

said inner transducer element being spherical and having its focal point on or close to the surface and detecting sound scattered and reradiated from surface discontinuities and cracks in said solid body while being insensitive to any reflected sound and reradiated waves.

2. The ultrasonic transducer of claim 1 wherein said outer transducer element is spherical and the angular extent is between an inner angle greater than said shear critical angle and an outer angle less than the Rayleigh critical angle where incident longitudinal waves are converted to surface waves, whereby incident longitudinal waves are totally reflected.

3. The ultrasonic transducer of claim 1 wherein said outer transducer element is spherical and the angular extent is between an inner angle greater than said shear critical angle and an outer angle greater than the Rayleigh critical angle where incident longitudinal waves are converted to surface waves that propagate inwardly along the surface of said solid body through the focus of said inner element.

4. The ultrasonic transducer of claim 3 wherein said inner and outer transducer elements are non-confocal and the focal point of said outer element is a short distance below the focal point of said inner element.

5. The ultrasonic transducer of claim 4 wherein the distance between the focal points of said inner and outer elements is determined by said Rayleigh critical angle and by selecting the diameter of a surface wave generation ring to be less than or equal to the Schoch displacement.

6. The ultrasonic transducer of claim 3 wherein said inner and outer transducer elements are confocal and coplanar.

7. The ultrasonic transducer of claim 1 wherein said annular outer transducer element is conical and generates plane waves which are incident on the surface of said solid body at an angle equal to or greater than the Rayleigh critical angle so that acoustic waves are converted to surface waves.

8. The ultrasonic transducer of claim 1 wherein said inner and outer transducer elements are comprised of poly vinylidene di fluoride piezoelectric film.

9. A dark field ultrasonic transducer system to detect the shape and crack depth profile of cracks in a part made of a solid, comprising:

an inner spherical detecting transducer element and a coaxial, annular, outer spherical transmitting transducer element;

said outer transducer element occupying an angular sector between an inner angle larger than the shear critical angle of said solid so that neither longitudinal nor shear waves are transmitted into said part, and an outer angle larger than the Rayleigh critical angle so that surface waves are generated on said part, said surface waves being scattered upon encountering a crack edge and reradiated as a first longitudinal wave and generating a surface wave which reflects from the bottom of said crack and returns to said crack edge and reradiates as a second longitudinal wave;

said inner transducer element detecting said first and second longitudinal waves radiated from said crack edge and generating voltage pulses; and means for determining the time delay between said pulses and thus crack depth at locations along the crack length as said transducer scans said part.

10. The ultrasonic transducer system of claim 9 wherein said outer transducer element generates a ring of said surface waves whose diameter is less than the Schoch displacement.

11. The ultrasonic transducer system of claim 9 wherein said inner and outer transducer elements are non-confocal.

12. The ultrasonic transducer system of claim 9 wherein said inner and outer transducer elements are confocal and coplanar.

13. A dark field ultrasonic transducer system to detect the shape and crack depth profile of cracks in a part, comprising:

an inner spherical detecting transducer element and a coaxial, annular, outer conical transmitting transducer element;

said outer transducer element emitting plane waves that are incident on the surface of said part at an angle equal to the Rayleigh critical angle so that surface waves are generated on said part and no acoustic waves are transmitted into said part, said surface waves being scattered upon encountering a crack edge and reradiated as a first longitudinal wave and generating a surface wave which reflects from the bottom of said crack and returns to said crack edge and reradiates as a second longitudinal wave;

said inner transducer element detecting said first and second longitudinal waves reradiated from said crack edge and generating voltage pulses; and means for determining the time delay between said pulses and thus crack depth at locations along the crack length as said transducer scans said part.

14. The ultrasonic transducer system of claim 13 wherein said outer transducer element generates a ring of said surface waves whose diameter is less than the Schoch displacement.

15. The ultrasonic transducer system of claim 13 wherein adjacent edges of said inner and outer transducer elements are coplanar.

* * * * *